(12) United States Patent
Tang et al.

(10) Patent No.: US 11,604,182 B2
(45) Date of Patent: Mar. 14, 2023

(54) APPARATUS AND METHOD FOR DETECTING GROUT COMPACTNESS IN GROUTED SPLICE SLEEVE

(71) Applicants: Guangzhou Municipal Engineering Testing Co., Ltd., Guangzhou (CN); Guangzhou Construction Engineering Co., Ltd., Guangzhou (CN); Guangzhou Municipal Construction Group Co., LTD., Guangzhou (CN)

(72) Inventors: Mengxiong Tang, Guangzhou (CN); Zhiguo Zhou, Guangzhou (CN); Xiaoli Sun, Guangzhou (CN); Hongye Wang, Guangzhou (CN); Jun Yang, Guangzhou (CN); Hesong Hu, Guangzhou (CN); Wuyang Zhou, Guangzhou (CN); Decun Bian, Guangzhou (CN); Yayu Zhao, Guangzhou (CN); Jixi Shao, Guangzhou (CN); Ducheng Guo, Guangzhou (CN); Hongbin Zhao, Guangzhou (CN)

(73) Assignees: GUANGZHOU MUNICIPAL ENGINEERING TESTING CO., LTD., Guangzhou (CN); GUANGZHOU CONSTRUCTION ENGINEERING CO., LTD., Guangzhou (CN); GUANGZHOU MUNICIPAL CONSTRUCTION GROUP CO., LTD., Guangzhou (CN)

( * ) Notice: Subject to any disclaimer, the term of this patent is extended or adjusted under 35 U.S.C. 154(b) by 157 days.

(21) Appl. No.: 17/122,287

(22) Filed: Dec. 15, 2020

(65) Prior Publication Data
US 2021/0349073 A1 Nov. 11, 2021

(30) Foreign Application Priority Data

May 9, 2020 (CN) .......................... 202010387644.6
May 9, 2020 (CN) .......................... 202010388646.7

(51) Int. Cl.
*G01N 33/38* (2006.01)
(52) U.S. Cl.
CPC .................................. *G01N 33/383* (2013.01)
(58) Field of Classification Search
CPC combination set(s) only.
See application file for complete search history.

(56) References Cited

U.S. PATENT DOCUMENTS

| 3,670,634 A | * | 6/1972 | Kessler | .................. G03B 7/083 |
| | | | | 396/293 |
| 4,788,488 A | * | 11/1988 | Kramer | ............. G01R 27/2605 |
| | | | | 73/304 C |

(Continued)

FOREIGN PATENT DOCUMENTS

| CN | 105223344 A | 1/2016 |
| CN | 107478512 A | 12/2017 |

(Continued)

OTHER PUBLICATIONS

Wikipedia Contributors. (May 3, 2020b). Smart device. Wikipedia. Retrieved Jun. 30, 2022, from https://web.archive.org/web/20200503014642/https://en.wikipedia.org/wiki/Smart_device (Year: 2020).*

(Continued)

*Primary Examiner* — Daniel R Miller
*Assistant Examiner* — Eric Sebastian Von Wald
(74) *Attorney, Agent, or Firm* — Muncy, Geissler, Olds & Lowe, P.C.

(57) ABSTRACT

Provided is an apparatus and method for detecting grout compactness in grouted splice sleeve, the apparatus com- (Continued)

prises a probe assembly, which comprises at least one of capacitive probe and piezoelectric sensor and is arranged inside the grouted splice sleeve to detect parameters of the sleeve during grouting and curing and a detector, which comprises at least an analysis module that is connected with the probe assembly to obtain the detected parameters and carry out calculation and analysis for the parameters. The probe assembly is arranged inside the grouted splice sleeve and forms a loop with the detector during grouting, such that during the process of grouting, the detected parameters will be changed as the surrounding dielectric changes, therefore, the detector may determine in real time whether the grouted splice sleeve is fully grouted by calculating and analyzing the detected parameters, which achieves a faster and easier grout compactness detection.

7 Claims, 8 Drawing Sheets

(56) References Cited

U.S. PATENT DOCUMENTS

| | | | | |
|---|---|---|---|---|
| 2013/0211795 | A1* | 8/2013 | Vanker | E04B 1/08 703/1 |
| 2018/0238820 | A1* | 8/2018 | Ghods | G01M 5/0083 |

FOREIGN PATENT DOCUMENTS

| | | | | | |
|---|---|---|---|---|---|
| CN | 109086519 | A | * | 12/2018 | |
| CN | 110068611 | A | * | 7/2019 | |
| CN | 110455678 | A | * | 11/2019 | G01N 9/00 |
| CN | 110455914 | A | | 11/2019 | |
| CN | 111075119 | A | * | 4/2020 | E04C 5/165 |
| KR | 101550267 | B1 | * | 9/2015 | |

OTHER PUBLICATIONS

Tianyong Jiang et al"Monitoring of Grouting Compactness in a Post-Tensioning Tendon Duct Using Piezoceramic Transducers." *Sensors* 16, No. 8: 1343; 2016 (13 pp.).

N. Li et al., "Portable System Design for inspecting Grouting Quality of Prestressed Ducts Based on a Coplanar Capacitive Sensor," Journal of Beijing University of Technology, 2016, 42(6): 809-818.

* cited by examiner

APPARATUS AND METHOD FOR DETECTING GROUT COMPACTNESS IN GROUTED SPLICE SLEEVE

CROSS REFERENCE TO RELATED APPLICATION

This application claims priorities of Application nos. 202010387644.6 and 202010388646.7 both filed in China on May 9, 2020, under U.S.C. § 119, the entire contents of which are hereby incorporated by reference.

TECHNICAL FIELD

The following relates to the field of construction quality detection, in particular to apparatus and method for detecting grout compactness in grouted splice sleeve.

BACKGROUND OF INVENTION

With the rapid development of domestic economy and urbanization, the building industrialization is also expedited. Conventional cast-in-place construction solutions have fallen short of the development needs for construction industry due to their disadvantages such as inappropriate resource allocation, low mechanization degree, and poor working environment. In recent years, prefabricated construction, which is a standardized and green architectural form having the advantages of rapid construction, energy saving, environment protection, and high quality, is therefore increasingly valued in the construction industry.

Seismic performance and integrality of the prefabricated construction are main factors affecting its development, therefore, reliable splices between the prefabricated construction members are required to improve the seismic performance and integrality of the prefabricated construction. Typically, splicing method of the prefabricated construction is grouted sleeve splicing of rebar, which can effectively ensure the integrality, and therefore improve the seismic performance of the prefabricated construction. The grouted sleeve splicing of rebar is widely used in architectural structures such as prefabricated shear wall for housing building, prefabricated box girder and bridge pier.

The rebar sleeve unit mainly comprises grouted splice sleeve and rebar for splicing of prefabricated construction members. Currently, the conventional methods for detecting the compactness of the grouting in the metal sleeve include unidirectional tensile test, high stress repeated tensile test and large deformation tensile test or the like, aiming at splice specimens of the metal sleeve. However, due to concealment of defects of the grouting in the sleeve, the conventional detecting methods cannot indicate the exact position of defects for reinforcement. As for nondestructive detecting methods, the methods using ultrasonic wave, impact-echo, or infrared thermal imaging cannot precisely detect and determine the defect position and the defect level of grouting in the sleeve, which realize relative low detection precision; the methods using x-ray CT can obtain high quality images clearly showing internal structure, compactness of the metal sleeve and distribution of the defects in grouting, which realize high precision for grout compactness detection, but the detecting apparatus is huge, complex and is of high cost. These methods further have disadvantages of radiations and environment pollutions, which are harmful to human beings, and that's why this method has not been widely used.

A method and apparatus for detecting grout compactness in grouted splice sleeve by drawing steel wire pre-embedded is disclosed in CN107478512A, specifically, extending the steel wire into the grouting outlet of the grouted splice sleeve and abuts against the rebar inside the grouted splice sleeve at the side approximate to the grout outlet prior to grouting, forming an anchoring segment, a grouting material barrier segment and a drawing segment sequentially from the end abutting against the rebar, then grouting in the sleeve and natural curing for 3 days, after that a center hole jack could be used to draw the embedded steel wire, and the compactness of the grouting can be indicated by the drawing load value. This method has the advantage of lower cost, but has the disadvantage that the detection cannot be performed until a 3-day curing procedure is finished after the grouting, therefore it cannot achieve real-time detection. As a result, the grout material may not be replenished in time since the grouting defects are not found during the grouting.

A method and apparatus for detecting grout compactness of rebar sleeve unit by pre-embedded sensor is disclosed in CN105223344A, specifically, a vibration sensor is pre-embedded below the grout outlet of the grouted splice sleeve, after the grouting is completed or the grout material is cured, the compactness of the grouting can be indicated by the amplitude attenuation of the detected signal of the sensor. This method cost higher, and the residual grout on the core component of the sensor may be cured and lead to an incorrect detection result, still, this method cannot achieve real-time detection during grouting because the detection cannot be performed until the grouting has been completed.

SUMMARY OF THE INVENTION

It is an objective of the invention to provide a method and apparatus for detecting grout compactness in grouted splice sleeve, which realize real-time detection during grouting process.

The objective is achieved by the following technical solutions:

An apparatus for detecting grout compactness in grouted splice sleeve, comprising
  A probe assembly, the probe assembly is arranged inside the grouted splice sleeve to detect parameters of the sleeve during grouting and curing;
  A detector, the detector is connected with the probe assembly to obtain the detected parameters and carry out calculation and analysis for the parameters.

The probe assembly comprises at least one of capacitive probe and piezoelectric sensor, which is arranged inside the grouted splice sleeve to detect parameters of the sleeve during grouting and curing; wherein,
  The probe assembly is inserted into the grouted splice sleeve through a first rubber plug at the top of the sleeve; or
  The probe assembly is inserted into the grouted splice sleeve through a second rubber plug at the grout outlet of the sleeve; or
  The probe assembly inserted into the grouted splice sleeve after being connected in parallel with the rebar.

The detector comprises at least an analysis module that is connected with the probe assembly to obtain the detected parameters and carry out calculation and analysis for the parameters. The analysis module comprises
  At least one time base circuit, which is connected to the probe assembly;
  At least one multi-vibrator, which is connected to the time base circuit; and At least one smart display, which is connected to the output of the time base circuit for displaying output parameters.

Preferably, the probe assembly comprises at least a capacitive probe for detecting the capacitance of the grouted splice sleeve during grouting;

The detector comprises at least a capacitance analysis module connected to the capacitive probe for calculation and analysis of the capacitance.

Further, the capacitance analysis module comprises

At least two time base circuits, which comprises a first time base circuit and a second time base circuit interconnected with each other, wherein the first time base circuit and the capacitive probe is connected to form a multi-vibrator;

A first multi-vibrator, which is connected to the second time base circuit to form a monostable trigger, wherein the second time base circuit outputs a current signal under the action of the first multi-vibrator and the monostable trigger; and A first smart display, which is connected to the output of the time base circuit for displaying value of the current output signal.

Alternatively, the probe assembly comprises at least a piezoelectric sensor for detecting stress level of the grouted splice sleeve during grouting;

the detector comprises at least a stress analysis module connected to the piezoelectric sensor for calculation and analysis of stress value.

Further, the stress analysis module comprises

A time base circuit, which is connected to the piezoelectric sensor for obtaining resonance frequency signal;

A second multi-vibrator, which is connected to the time base circuit, wherein the time base circuit outputs a voltage signal according to the resonance frequency signal under the action of the second multi-vibrator; and A second smart display, which is connected to the output of the time base circuit for displaying value of the voltage output signal.

Further, the detector also comprises

A memory unit for storing various parameters;

A coding device for creating and scanning a QR code;

A printing module, which is connected to the memory unit and the coding device for printing the QR code and the parameters;

An algorithm circuit module, which is connected to the memory unit for accessing the parameters for calculating grouting compactness distribution data in the grouted splice sleeve during grouting and curing;

A 3-dimensional (3D) graphics display module, which is connected to the algorithm circuit module for accessing and displaying the grouting compactness distribution data in 3D graphics; and A wireless data transmission module, which is connected to the 3D graphics display module for wirelessly transmitting the 3D graphics of the grouting compactness distribution data to a mobile device or a computer.

The present invention may further comprise a metal hose configured for housing the probe assembly.

Further, the probe assembly may be subjected to sandblasting with 200-400 mesh irregular quartz sand.

Further, the probe assembly may have a coating made from hydrophobic material, i.e. modified polysilazane material; wherein the modified polysilazane material comprises 10 parts by weight of polysilazane, 0.4 parts by weight of silane coupling agent, 0.2 parts by weight of silica, and 0.08 parts by weight of perfluoropolyether.

A method for detecting grout compactness in grouted splice sleeve is further provided, comprising the following steps, Providing a probe assembly comprising at least one of capacitive probe and piezoelectric sensor; inserting the probe assembly into the grouted splice sleeve with the at least one of capacitive probe and piezoelectric sensor arranged inside the grouted splice sleeve to detect parameters of the sleeve during grouting and curing; wherein inserting the probe assembly into the grouted splice sleeve may further comprise at least one of the following steps, Inserting the probe assembly into the grouted splice sleeve through a first rubber plug at the top of the grouted splice sleeve; or Inserting the probe assembly into the grouted splice sleeve through a second rubber plug at the grout outlet of the grouted splice sleeve; or Inserting the probe assembly connected in parallel with the rebar into the grouted splice sleeve.

Providing a predetermined threshold range on a detector, the detector comprises at least an analysis module that is connected with the probe assembly to obtain the detected parameters and carry out calculation and analysis for the parameters; wherein the analysis module comprises at least a time base circuit connected to the probe assembly;

at least a multi-vibrator connected to the time base circuit; and at least a smart display connected to the output of the time base circuit for displaying output parameter;

Obtaining the parameters of the grouted splice sleeve by the detector during grouting and curing;

Comparing the detected parameter with the threshold range, the grouted splice sleeve will be determined as fully grouted if the detected parameter is within the threshold range, whereas the grouted splice sleeve will be determined as defectively grouted if the detected parameter is out of the threshold range.

Preferably, the probe assembly comprises at least a capacitive probe, the parameter to be detected is a capacitance, and the threshold range is a threshold range of the capacitance value; the detector comprises at least a capacitance analysis module connected to the capacitive probe, the method further comprises steps of determining the threshold range, including Calculating the permittivity of the grout;

Obtaining an estimated capacitance value by calculation on the basis of the permittivity;

Obtaining a measured capacitance value detected by the capacitive probe after the grouted splice sleeves are grouted; and Determining the threshold range in consideration of the calculated capacitance value and the measured capacitance value.

According to another aspect of the application, inserting the probe assembly into the grouted splice sleeve may further comprise at least one of the following steps:

Inserting the capacitive probe into the grouted splice sleeve through a first rubber plug at the top of the grouted splice sleeve; or Inserting the capacitive probe into the grouted splice sleeve through a second rubber plug at the grout outlet of the grouted splice sleeve; or Connecting the capacitive probe in parallel with the rebar inside the grouted splice sleeve and inserting the capacitive probe into the grouted splice sleeve.

Alternatively, the probe assembly comprises at least a piezoelectric sensor, the parameter to be detected is a stress value, and the threshold range is a threshold range of the stress value; the detector comprises at least a stress analysis module connected to the piezoelectric sensor, the method further comprises steps of determining the threshold range, including Obtaining an estimated resonance frequency by calculation after the piezoelectric sensor has been in contact with the grout;

Obtaining a measured resonance frequency detected by the piezoelectric sensor after the grouted splice sleeves are grouted;

Determining the threshold range of the resonance frequency in consideration of the estimated resonance frequency and the measured resonance frequency; and Determining the threshold range of the stress value by converting the threshold range of the resonance frequency.

According to another aspect of the application, inserting the probe assembly into the grouted splice sleeve further comprises at least one of the following steps:

Inserting the piezoelectric sensor into the grouted splice sleeve through a first rubber plug at the top of the grouted splice sleeve; or Inserting the piezoelectric sensor into the grouted splice sleeve through a second rubber plug at the grout outlet of the grouted splice sleeve; or Connecting the piezoelectric sensor in parallel with the rebar inside the grouted splice sleeve and inserting the piezoelectric sensor into the grouted splice sleeve.

According to a further aspect of the application, the grouted splice sleeve may be considered as fully grouted under the following conditions, including The detected parameter value is within the threshold range when grouting is finished; or The detected parameter value is within the threshold range when grouting is finished, but later it is restored to its level before grouting; Whereas the grouted splice sleeve may be considered as defectively grouted under the following conditions, including The detected parameter value is out of the threshold range when grouting is finished.

According to a further aspect of the application, inserting the probe assembly into the grouted splice sleeve further comprises at least one of the following steps:

Prefabricating the probe assembly pre-embedded in the grouted splice sleeve prior to grouting; or Inserting the probe assembly into the grouted splice sleeve during grouting.

As compared with the prior art, the present invention is advantageous in that the probe assembly is arranged inside the grouted splice sleeve and forms a loop with the detector during grouting, such that during the process of grouting, the detected parameters will be changed as the surrounding dielectric changes, therefore, the detector may determine in real time whether the grouted splice sleeve is fully grouted by calculating and analyzing the detected parameters, which achieves a faster and easier grout compactness detection.

BRIEF DESCRIPTION OF DRAWINGS

The present invention will be described hereinafter in details with reference to the figures and the embodiments, wherein.

LIST OF REFERENCE CHARACTERS

Figure 1:
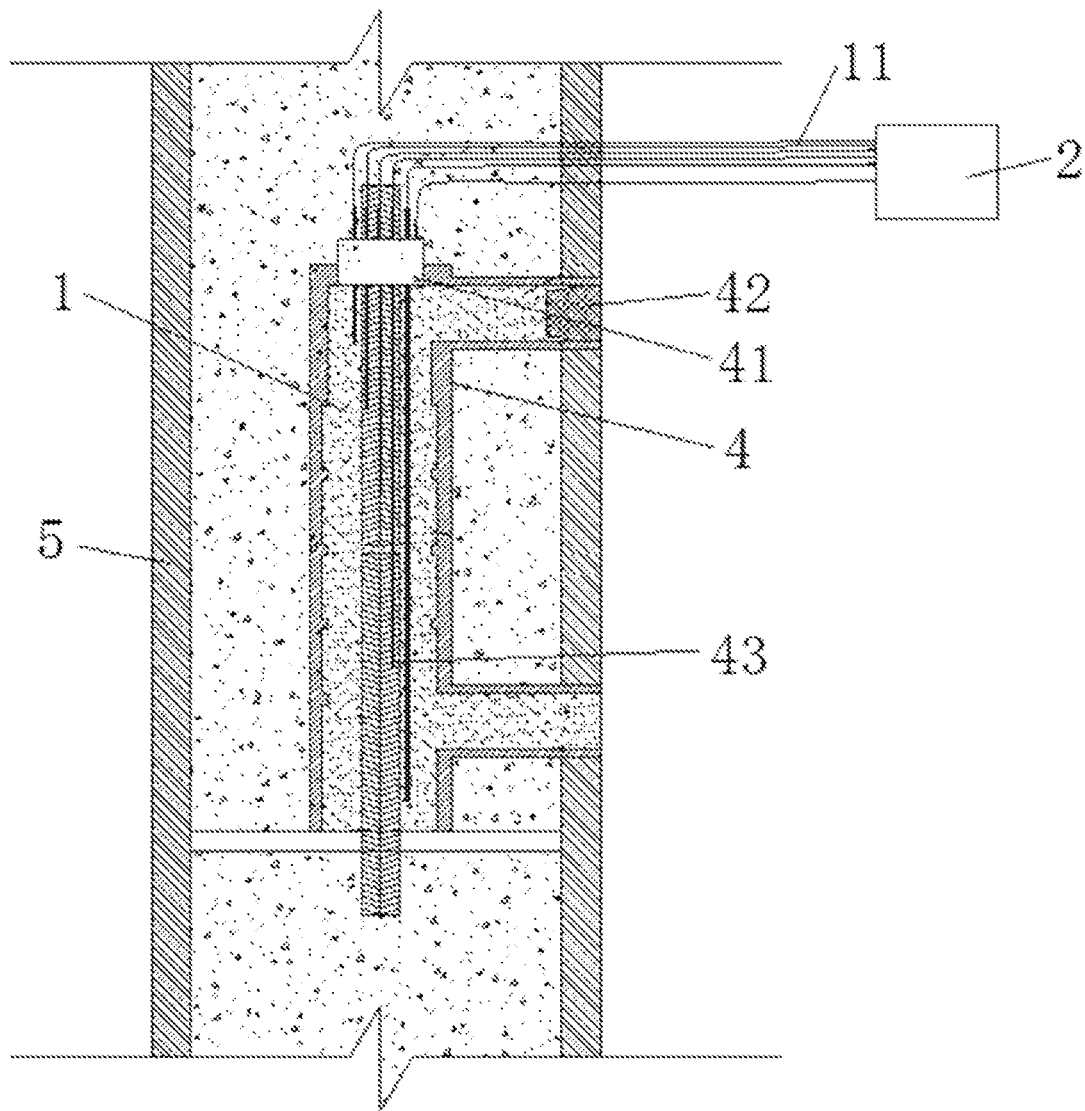
FIG. 1 illustrates an apparatus for detecting grout compactness in grouted splice sleeve in use according to embodiment 1 and embodiment 2 of the present invention.

1 Probe assembly
11 Hipot, anti-corrosion, and waterproof cable
2 Detector
21 Capacitance analysis module
211 Dual time base circuit
2111 First time base circuit
2112 Second time base circuit
212 First multi-vibrator
213 First smart display
22 Stress analysis module
221 Time base circuit
222 Second multi-vibrator
223 Second smart display
23 Memory unit
24 Coding device
25 Printing module
26 Algorithm circuit module
27 3-dimensional (3D) graphics display module
28 Wireless data transmission module
4 Grouted splice sleeve
41 First rubber plug
42 Second rubber plug
43 Spliced rebar
5 Pouring template

DETAILED DESCRIPTION OF THE INVENTION

The invention will be described in more details hereinafter with reference to the figures and embodiments. It should be noted that the embodiments described hereinafter are merely preferred embodiments of the present invention and not for purposes of any restrictions or limitations to the invention.

Embodiment 1

As shown in FIG. 1, the embodiment provides an apparatus for detecting grout compactness in grouted splice sleeve 4, which comprises a probe assembly 1 arranged inside the grouted splice sleeve 4 for detecting parameters of the grouted splice sleeve 4 during grouting and curing and a detector 2 connected with the probe assembly 1 to obtain the detected parameters and carry out calculations and analysis for the parameters.

In this embodiment, the probe assembly 1 comprises at least one capacitive probe $C_x$ to detect capacitance in the grouted splice sleeve 4 during grouting; the detector 2 comprises at least one capacitance analysis module 21 connected to the capacitive probe $C_x$ for calculation and analysis of the capacitance.

In this embodiment, the capacitance analysis module 21 comprises a dual time base circuit 211 comprising a first time base circuit 2111 and a second time base circuit 2112 interconnected with each other, a first multi-vibrator 212, and a first smart display, wherein the first time base circuit 2111 is connected to the capacitive probe $C_x$ and forms a multi-vibrator; the first multi-vibrator 212 is connected to the second time base circuit 2112 and forms a monostable trigger; the second time base circuit 2112 outputs a current signal under the action of the first multi-vibrator 212 and the monostable trigger, and the first smart display is connected to the output of the first time base circuit 2111 for displaying value of the current output signal.

Figure 2:
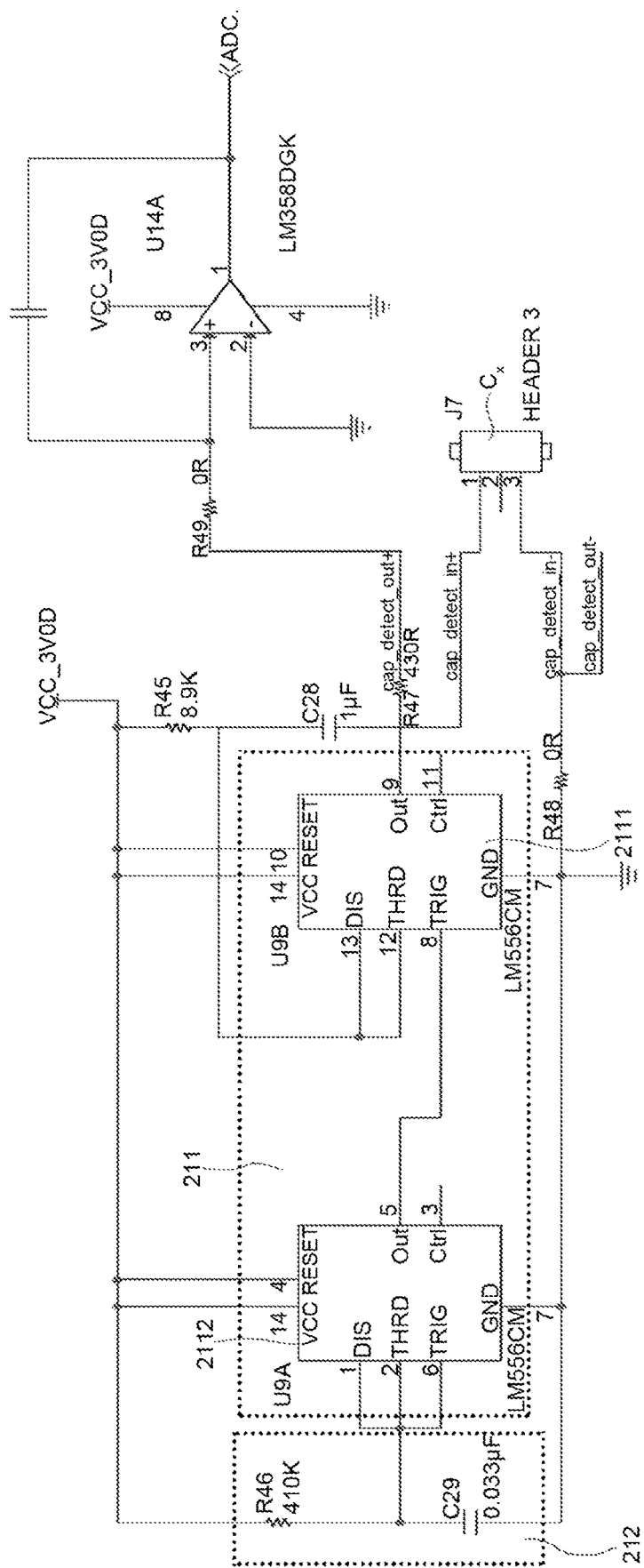
FIG. 2 illustrates a circuit diagram of a capacitance analysis module according to embodiment 1 of the present invention.

Specifically, as shown in FIG. 2, the dual time base circuit 211 may comprise a LM556 chip, wherein the second time base circuit 2112 is the 555 circuit on the left half. $R_{46}C_{29}$ make up the first multi-vibrator 212 with 50% duty cycle, of which the oscillation frequency may be determined as $f=1.44/(R_1C_1)$, then the oscillation frequency f can be calculated according to the parameters of elements shown in FIG. 2 as $f=1.44/(414 \times 10^3 \times 0.033 \times 10^{-6})=105$ Hz; the first time base circuit 2111 is the 555 circuit on the right half, together with the capacitive probe $C_x$ forming a monostable trigger, wherein the pulse width of the monostable trigger may be determined as $t_d=1.1R_{45}C_x$, and the pulse width $t_d$ can be calculated according to the parameters of elements given in FIG. 2 as $t_d=10^4 C_x$. The current I, which varies with the capacitance value of capacitive probe $C_x$, may output from the pin 9 of the LM556 chip to be transferred into an average DC current by a current-limit resistance $R_{47}$, and output to the first smart display 223, by which the current value may be converted to a capacitance value.

Figure 3:
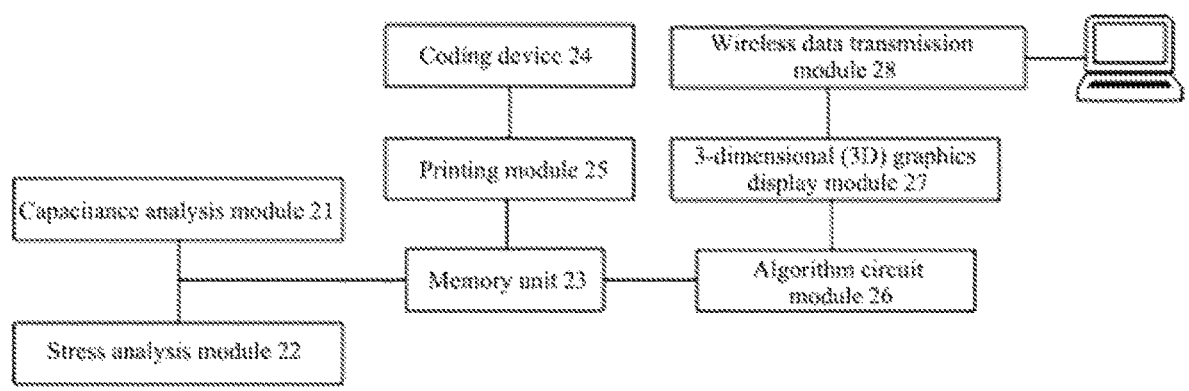
FIG. 3 illustrates a structure diagram of a detector according to embodiment 1 of the present invention.

As shown in FIG. 3, the detector 2 in this embodiment further comprises a memory unit 23 for storing various parameters, a coding device 24 for creating and scanning a QR code, a printing module 25 connected to the memory unit 23 and the coding device 24 for printing the QR code and the parameters, an algorithm circuit module 26 connected to the memory unit 23 for accessing the parameters for calculating grouting compactness distribution data in the grouted splice sleeve 4 during grouting and curing, a 3-dimensional (3D) graphics display module 27 connected to the algorithm circuit module 26 for accessing and displaying the grouting compactness distribution data in 3D graphics, and a wireless data transmission module 28 connected to the 3D graphics display module 27 for wirelessly transmitting the 3D graphics of the grouting compactness distribution data to a mobile device or a computer.

Figure 4:
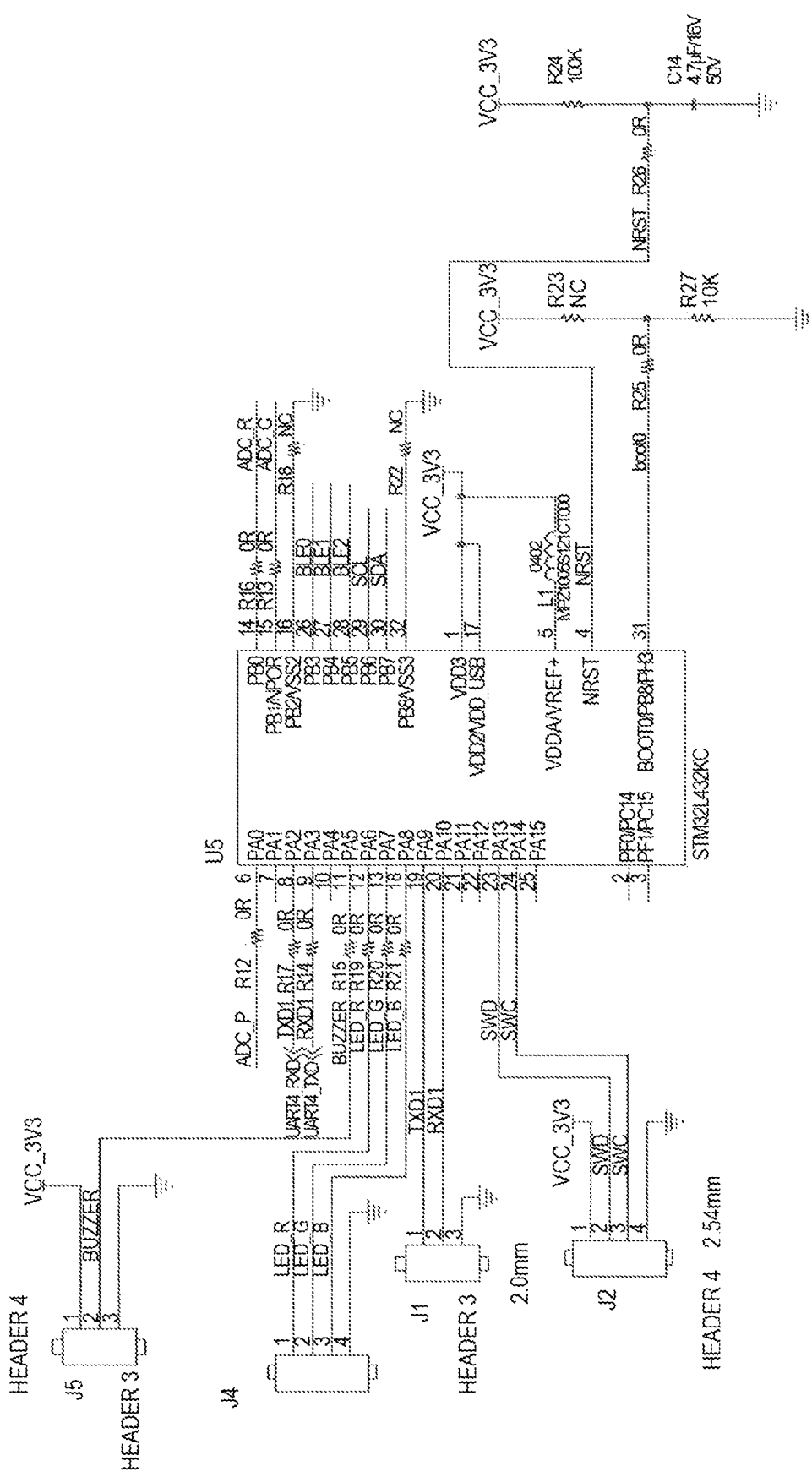
FIG. 4 illustrates a circuit diagram of a microcontroller unit according to embodiment 1 and embodiment 2 of the present invention.
Figure 5:
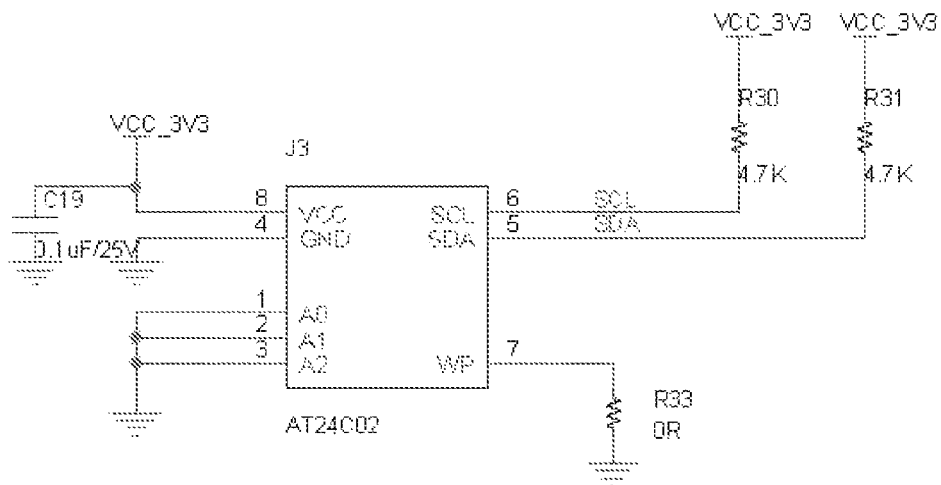
FIG. 5 illustrates a circuit diagram of a memory unit according to embodiment 1 and embodiment 2 of the present invention.
Figure 6:
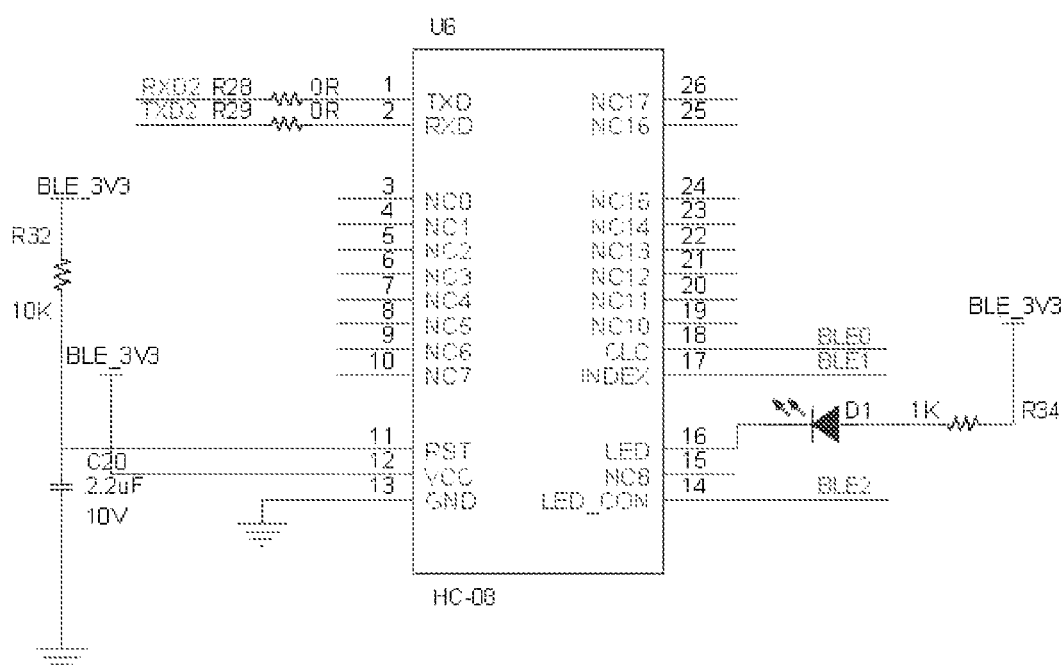
FIG. 6 illustrates a circuit diagram of a wireless data transmission module according to embodiment 1 and embodiment 2 of the present invention.

As shown in FIG. 4, a microcontroller unit could be used instead of the first smart display and the algorithm circuit module 26. A buzzer and/or an indicator may be further provided to indicate the working state of the detecting apparatus. FIG. 5 illustrates circuit diagram of the memory unit 23, and FIG. 6 illustrates the wireless data transmission module 28.

Before detection, each prefabricated member is tagged with a QR code by the coding device 24. When a defectively grouted splice sleeve 4 is detected, the respective QR code could be scanned by the coding device 24 for recording and saving location data for subsequent reinforcement.

A metal hose (not shown) may be further configured for housing the probe assembly in this embodiment, such that the capacitive probe $C_x$ can be reused. The metal hose penetrates the pouring template 5 and extends into the interior of the grouted splice sleeve 4. The capacitive probe is arranged inside the metal hose and connected to the detector 2 via a cable 11 that have properties of hipot, anti-corrosion, and waterproof.

Further, the probe assembly 1 in this embodiment may be subjected to sandblasting with 200-400 mesh irregular quartz sand.

Further, the probe assembly 1 in this embodiment may have a coating made from hydrophobic material, which means, the probe assembly 1 is coated with hydrophobic material except for its tip. The hydrophobic material is modified polysilazane material, which comprises 10 parts by weight of polysilazane, 0.4 parts by weight of silane coupling agent, 0.2 parts by weight of silica, and 0.08 parts by weight of perfluoropolyether.

Embodiment 2

This embodiment provides another apparatus for detecting grout compactness in grouted splice sleeve 4, which comprises a probe assembly 1 arranged inside the grouted splice sleeve 4 for detecting parameters of the grouted splice sleeve 4 during grouting and curing and a detector 2 connected with the probe assembly 1 to obtain the detected parameters and carry out calculation and analysis for the parameters. The probe assembly 1 comprises at least one piezoelectric sensor r for detecting stress level in the grouted splice sleeve 4 during grouting; the detector 2 comprises at least one stress analysis module 22 connected to the piezoelectric sensor for calculation and analysis of stress value.

Figure 7:
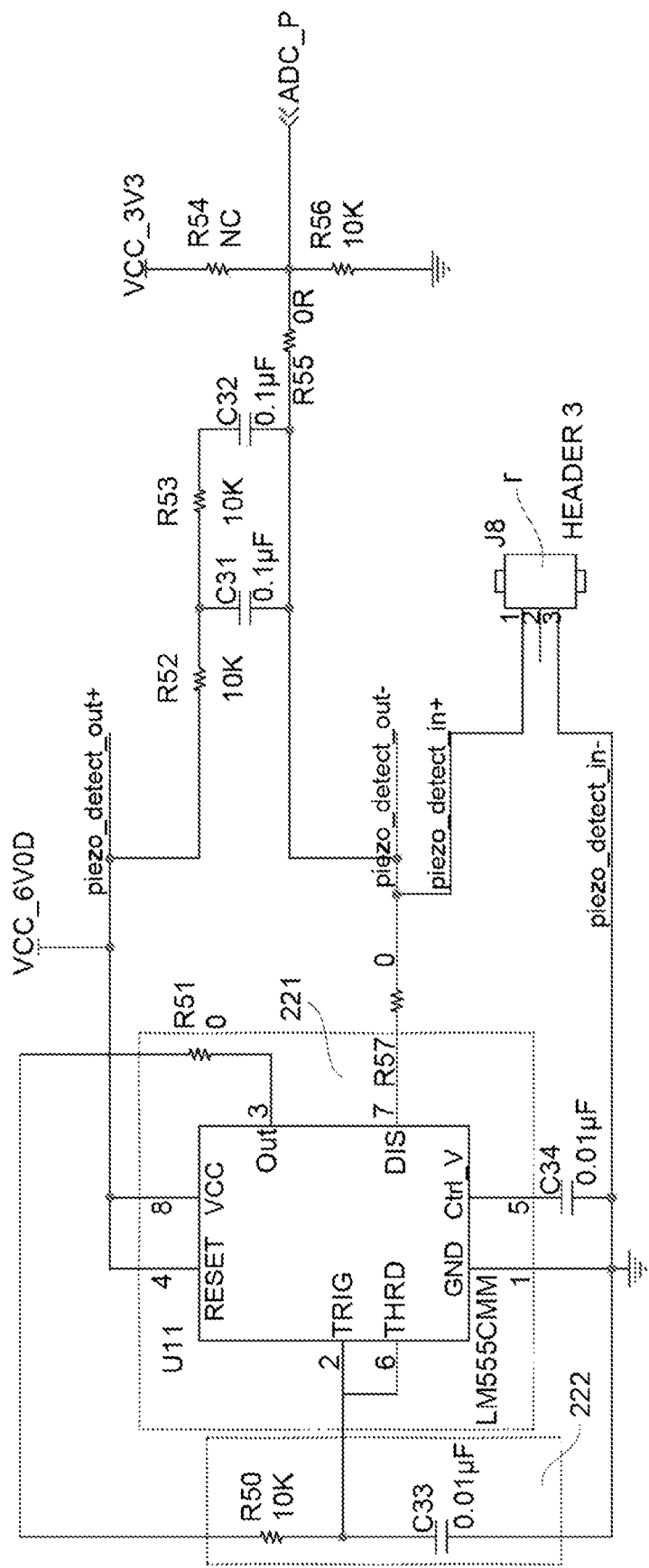
FIG. 7 illustrates a circuit diagram of a stress analysis module according to embodiment 2 of the present invention.

As shown in FIG. 7, the stress analysis module 22 comprises a time base circuit 221 connected to the piezoelectric sensor r for obtaining resonance frequency signal; a second multi-vibrator 222 connected to the time base circuit 221 for outputting a voltage signal according to the resonance frequency signal under the action of the second multi-vibrator 222; and a second smart display connected to the output of the time base circuit 221 for displaying value of the voltage output signal.

Specifically, the time base circuit 221 is a LM 555 time base circuit which outputs a voltage that can be converted to a stress value by the second smart display. The output of the second multi-vibrator 222 comprised of $R_{50}C_{33}$ is connected to the piezoelectric sensor r, wherein the oscillation frequency may be determined in the same way as that in embodiment 1, but the value is not necessarily equal to oscillation frequency $f_0$ of the piezoelectric sensor. The output value may rise sharply back to the original value after the piezoelectric sensor get in contact with the grout. Tests have shown that $\Delta V \geq 1V$ on basis of the parameters given in the FIG. 7.

The detector 2 in this embodiment further comprises a memory unit 23 for storing various parameters, a coding device 24 for creating and scanning a QR code, a printing module 25 connected to the memory unit 23 and the coding device 24 for printing the QR code and the parameters, an algorithm circuit module 26 connected to the memory unit 23 for accessing the parameters for calculating grouting compactness distribution data in the grouted splice sleeve 4 during grouting and curing, a 3-dimensional (3D) graphics display module 27 connected to the algorithm circuit module 26 for accessing and displaying the grouting compactness distribution data in 3D graphics, and a wireless data transmission module 28 connected to the 3D graphics display module 27 for wirelessly transmitting the 3D graphics of the grouting compactness distribution data to a mobile device or a computer.

As shown in FIG. 4, a microcontroller unit could be used instead of the first smart display and the algorithm circuit module 26. A buzzer and/or an indicator may be further provided to indicate the working state of the detecting apparatus. FIG. 5 illustrates circuit diagram of the memory unit 23, and FIG. 6 illustrates the wireless data transmission module 28.

Before detection, each prefabricated member is tagged with a QR code by the coding device 24. When a defectively grouted splice sleeve 4 is detected, the respective QR code could be scanned by the coding device 24 for recording and saving location data for subsequent reinforcement.

A metal hose may be further configured for housing the probe assembly in this embodiment, such that the piezoelectric sensor r can be reused. The metal hose penetrates the pouring template 5 and extends into the interior of the grouted splice sleeve 4. The piezoelectric sensor r is arranged inside the metal hose and connected to the detector 2 via a cable 11 that have properties of hipot, anti-corrosion, and waterproof.

Further, the probe assembly 1 in this embodiment may be subjected to sandblasting with 200-400 mesh irregular quartz sand.

Embodiment 3

Figure 8:
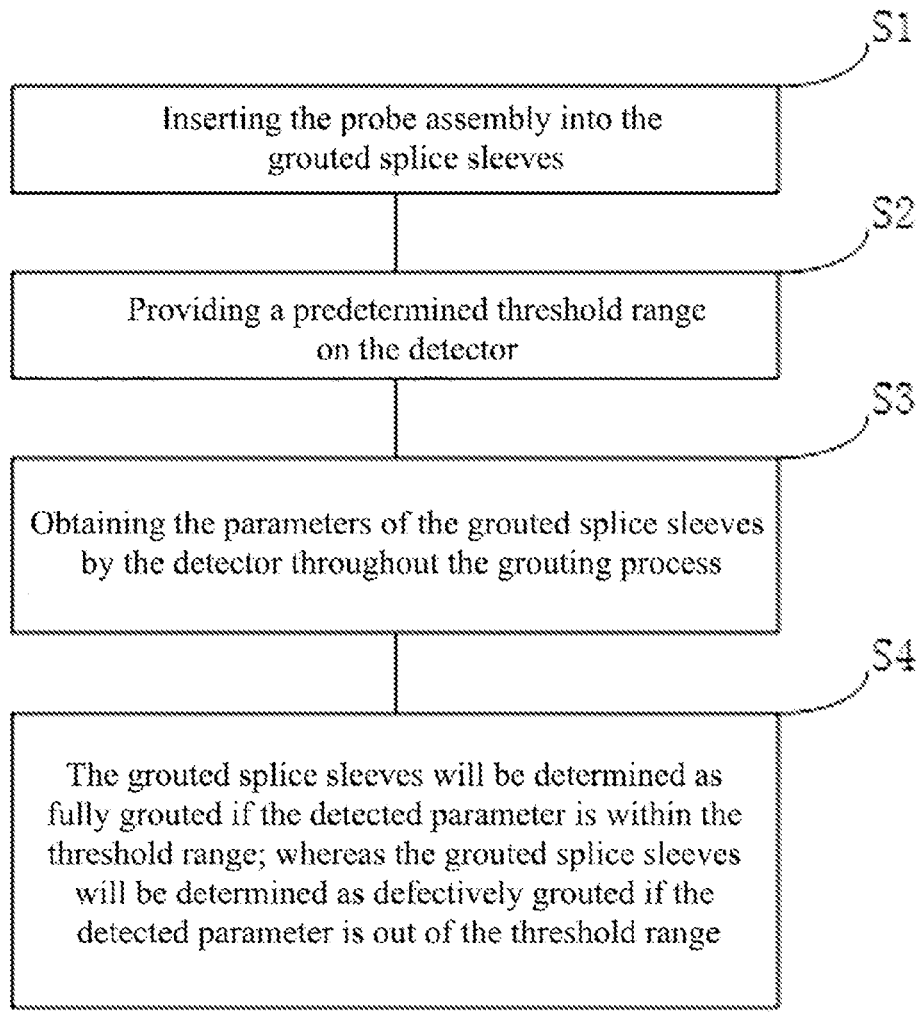
FIG. 8 illustrates a block diagram of a detecting method according to embodiment 3 and embodiment 4 of the present invention.

A method for detecting grout compactness in grouted splice sleeve 4 is further provided in this embodiment. As shown in FIG. 8, the method comprises the following steps, S1. Inserting the probe assembly 1 into the grouted splice sleeves 4;

S2. Providing a predetermined threshold range on the detector 2;

S3. Obtaining the parameters of the grouted splice sleeves 4 by the detector 2 throughout the grouting process;

S4. Comparing the detected parameter with the threshold range, the grouted splice sleeves 4 will be determined as fully grouted if the detected parameter is within the threshold range, whereas the grouted splice sleeves 4 will be determined as defectively grouted if the detected parameter is out of the threshold range.

The probe assembly 1 in this embodiment comprises at least a capacitive probe, the parameter to be detected is a capacitance, and the threshold range is a threshold range of the capacitance value; the detector 2 comprises at least a capacitance analysis module connected to the capacitive probe, the method further comprises steps of determining the threshold range, including Calculating the permittivity of the grout;

Obtaining an estimated capacitance value by calculation on the basis of the permittivity;

Obtaining a measured capacitance value detected by the capacitive probe after grouted splice sleeves 4 are grouted; and Determining the threshold range in consideration of the estimated capacitance value and the measured capacitance value.

Specifically, the grout is a non-conductor and its capacitance can be measured, the permittivity the mixture of cement, aggregate and mortar, which is a mixture of three phases including a solid, liquid and gaseous phase, may be calculated by the following equation (1)

$$\varepsilon_m = \left[\sum\nolimits_{n'}^{3} V_{n'}^2 \varepsilon_{n'}^2 + 4\sum\nolimits_{m=2}^{3} VV_{n'} \frac{\varepsilon_{m-1}V\varepsilon_{n'}}{\varepsilon_{m-1}\varepsilon_n}\right][1 + 20T \propto_\varepsilon] + b \quad (1)$$

Where $\varepsilon_{m3}$ and $V_{m3}$ are the permittivity and the corresponding volumetric concentration of each composition, respectively, T is temperature, and $\propto_\varepsilon$ is the temperature coefficient of permittivity, wherein the temperature coefficient of permittivity for water is $\propto_\varepsilon = -0.29/°$ C.

Materials in solid phase make hardly any difference to the permittivity E, but water will lead to an increased E, so that the permittivity E may be used to indicate the moisture content.

In a solid level detection for viscous materials, a sleeve structure with central insulating electrode is used in order to prevent the failure of detecting drop of grout level due to electrode adhesion, wherein the total capacitance value may be determined as following equation (2), $$C_x = C_0 + \frac{2\pi\varepsilon_1\varepsilon_3 H_0}{\varepsilon \ln(D/D_1) + \varepsilon_3 \ln(D_1/b)} + \frac{2\pi\varepsilon_1^2(D/D_1)}{\varepsilon_2 \ln(D/D_1) + \varepsilon_3 \ln(D_1/D_1)\ln(D/D_1)} = C_0 + KH_i \quad (2)$$

Where the $\varepsilon_1$, $\varepsilon_2$, $\varepsilon_3$ are insulation, dielectric and air respectively; $C_0$ is stray capacitance, which can be equivalent to a pure capacitance at low frequency. As the central electrode can't be made thin enough to produce substantial difference in capacitance of the grouted splice sleeve, the present invention uses non-central-electrode insulation, in which case the resistance is the conduction resistance of water, and the insulation of a capacitor is merely a single molecule of water, whose diameter $d=4\times10^{-7}$ cm, such that the capacitance can be very large and the value may be calculated by the following equation (3)

$$C = \frac{\varepsilon_r \varepsilon_0 A}{d} \quad (3)$$

Where C is the capacitance measured in pF;

$$\varepsilon_0 = \frac{\pi}{3.6}$$

is the vacuum permittivity; $\varepsilon_r = 8$ is the relative permittivity of water; A is the area, and d is the distance.

$$C = \frac{8 \times \pi \times 7 \times 10^{-3}}{3.6 \times 0.4 \times 10^{-7}} = 122 \times 10^4 pf = 1.22 \ \mu F \quad (4)$$

Experiments have shown that, planar electrode with a diameter of 1 mm has a capacitance of 20 μF, while a plastic capacitor which has the permittivity $\varepsilon_r$=2.3, the same area and the same thickness of insulation has a capacitance of only 0.02% to the foresaid capacitance of the planar electrode, in this way, the ratio of signal to noise is greatly improved and the detection circuit is simplified.

The method in this embodiment, inserting the probe assembly 1 into the grouted splice sleeve 4 may further comprise at least one of the following steps:

Inserting the capacitive probe into the grouted splice sleeve 4 through a first rubber plug 41 at the top of the grouted splice sleeve 4; or Inserting the capacitive probe into the grouted splice sleeve 4 through a second rubber plug 42 at the grout outlet of the grouted splice sleeve 4; or Connecting the capacitive probe in parallel with the rebar 43 inside the grouted splice sleeve 4, and inserting the capacitive probe into the grouted splice sleeve 4.

The grouted splice sleeve 4 may be considered as fully grouted under the following conditions, including:

The detected parameter value is within the threshold range when grouting is finished; or The detected parameter value is within the threshold range when grouting is finished, but later it is restored to its level before grouting;

Whereas the grouted splice sleeve 4 may be considered as defectively grouted under the following conditions, including:

The detected parameter value is out of the threshold range when grouting is finished.

In the method according to this embodiment, inserting the probe assembly into the grouted splice sleeve may further comprise the following steps:

Prefabricating the probe assembly 1 pre-embedded in the grouted splice sleeve 4 prior to grouting; or Inserting the probe assembly into the grouted splice sleeve 4 during grouting.

Embodiment 4

A method for detecting grout compactness in grouted splice sleeves 4 is further provided in this embodiment. As shown in FIG. 8, the method comprises the following steps, S1'. Inserting the probe assembly 1 into the grouted splice sleeves 4;

S2'. Providing a predetermined threshold range on the detector 2;

S3'. Obtaining the parameter of the grouted splice sleeves 4 by the detector 2 throughout the grouting process;

S4'. Comparing the detected parameter with the threshold range, the grouted splice sleeves 4 will be determined as fully grouted if the detected parameter is within the threshold range, whereas the grouted splice sleeves 4 will be determined as defectively grouted if the detected parameter is out of the threshold range.

In this embodiment, the threshold range is a threshold range of the stress value; the method further comprises steps of determining the threshold range, including Obtaining an estimated resonance frequency value by calculation after the piezoelectric sensor has been in contact with the grout;

Obtaining a measured resonance frequency detected by the piezoelectric sensor after the grouted splice sleeves 4 are grouted;

Determining the threshold range of the resonance frequency in consideration of the estimated resonance frequency and the measured resonance frequency; and Determining the threshold range of the stress value by converting the threshold range of the resonance frequency.

Figure 9:
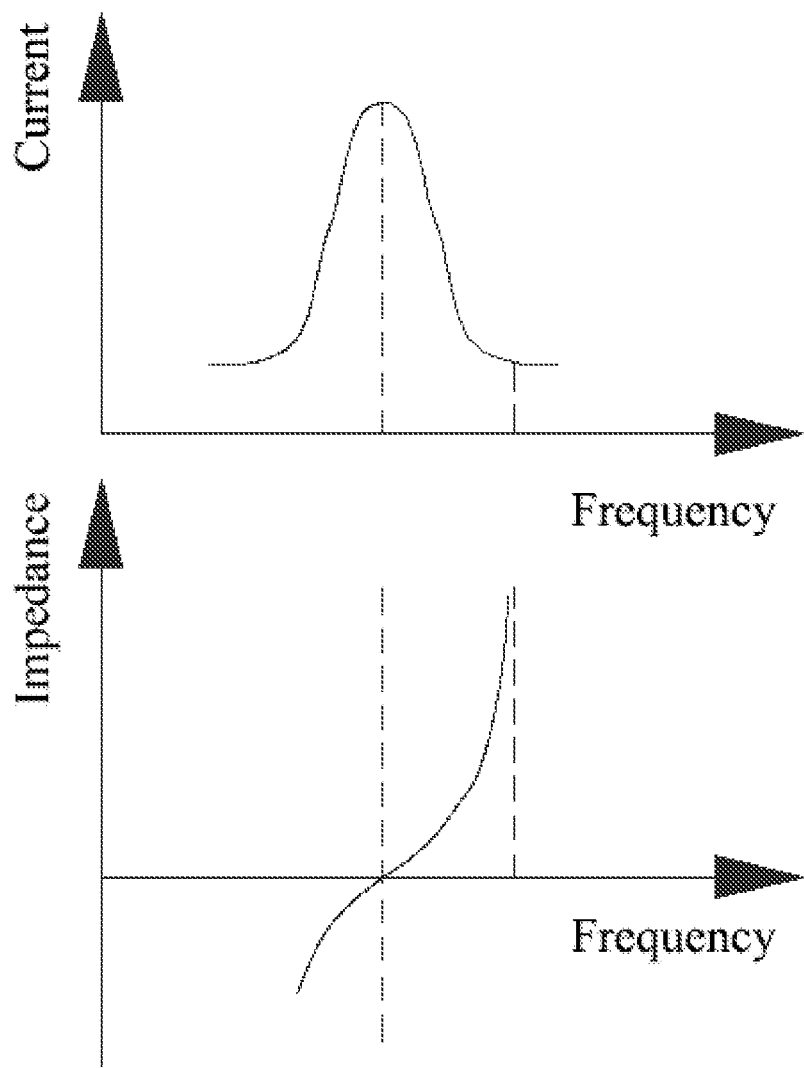
FIG. 9 illustrates a characteristic graph of current and impedance for a piezoelectric sensor according to embodiment 4 of the present invention.

Specifically, the piezoelectric sensor may directly obtain the value of the voltage across the piezoelectric element being contact with the viscous grout during resonance oscillation to determine whether contact occurs. As external excitation is not necessary, the processing circuit is greatly simplified and its cost is reduced. The resonance equivalent circuit and characteristic graph of current and impedance for the piezoelectric element are shown in FIG. 9, wherein the series resonance frequency $f_0$ and the parallel resonance frequency $f_1$ are respectively determined as $$\left.\begin{array}{l} f_0 = \dfrac{1}{2\pi\sqrt{LC}} \\ f_1 = \dfrac{1}{2\pi\sqrt{L(C//C)}} \end{array}\right\} \quad (5)$$

The contact between the probe assembly and the grout can be identified by detecting the voltage drop across the element caused by grout adhesion.

Moreover, the viscosity value of the detected material may be further determined by detecting the frequency offsets influenced by the grout adhesion and damping.

$$\Delta f = \Delta f_m + \Delta f_L = \frac{-2f_0^2 \rho}{N\sqrt{\mu\rho}} = -\frac{f_0^{3/2}}{N}\sqrt{\frac{\rho\eta_t}{\pi\mu\rho}} \quad (6)$$

Where $f_m$, and $f_L$ are frequency offsets influenced by the grout adhesion and damping, respectively; $f_0$ is the series resonance frequency; N is the harmonic order, and the $\rho$ and $\mu$ are the density and viscosity of the liquid, respectively.

The method in this embodiment, inserting the probe assembly 1 into the grouted splice sleeve 4 may further comprise at least one of the following steps:

Inserting the piezoelectric sensor into the interior of the grouted splice sleeve 4 through a first rubber plug 41 at the top of the grouted splice sleeve 4; or Inserting the piezoelectric sensor into the interior of the grouted splice sleeve 4 through a second rubber plug 42 at the grout outlet of the grouted splice sleeve 4; or Connecting the piezoelectric sensor in parallel with the rebar 43 inside the grouted splice sleeve 4 and inserting the piezoelectric sensor into the grouted splice sleeve 4.

The grouted splice sleeve 4 may be considered as fully grouted under the following conditions, including The detected parameter value is within the threshold range when grouting is finished; or The detected parameter value is within the threshold range when grouting is finished, but later it is restored to its level before grouting; Whereas the grouted splice sleeve 4 may be considered as defectively grouted under the following conditions, including:

The detected parameter value is out of the threshold range when grouting is finished.

In the method according to this embodiment, inserting the probe assembly into the grouted splice sleeve may further comprise the following steps:

Prefabricating the probe assembly 1 pre-embedded in the grouted splice sleeve 4 prior to grouting; or Inserting the probe assembly into the grouted splice sleeve 4 during grouting.

The embodiment described hereinbefore is merely preferred embodiment of the present invention and not for purposes of any restrictions or limitations on the invention. It will be apparent that any non-substantive, obvious alterations or improvement by the technician of this technical field according to the present invention may be incorporated into ambit of claims of the present invention.

What is claimed is:

1. An apparatus for detecting grout compactness in a grouted splice sleeve, comprising
   a probe assembly, wherein the probe assembly comprises at least a capacitive probe for detecting a capacitance of the grouted splice sleeve during grouting and is arranged inside the grouted splice sleeve to detect capacitance of the sleeve during grouting and curing; wherein the probe assembly have a coating made from hydrophobic material, i.e. modified polysilazane material; wherein the modified polysilazane material comprises 10 parts by weight of polysilazane, 0.4 parts by weight of silane coupling agent, 0.2 parts by weight of silica, and 0.08 parts by weight of perfluoropolyether;
   a first rubber plug at a top of the grouted splice sleeve;
   a second rubber plug at a grout outlet of the grouted splice sleeve;
   a rebar inside the grouted splice sleeve; wherein,
   the probe assembly is inserted into the grouted splice sleeve through the first rubber plug at the top of the sleeve; or
   the probe assembly is inserted into the grouted splice sleeve through the second rubber plug at the grout outlet of the sleeve; or
   the probe assembly is inserted into the grouted splice sleeve after being connected in parallel with the rebar; and
   a detector, wherein the detector comprises at least a capacitance analysis module connected to the capacitive probe, for calculation and analysis of the capacitance; wherein, the capacitance analysis module comprises
   at least two time base circuits, which comprises a first time base circuit and a second time base circuit interconnected with each other, wherein the first time base circuit and the capacitive probe is connected to form a multi-vibrator;
   a first multi-vibrator, which is connected to the second time base circuit to form a monostable trigger, wherein the second time base circuit outputs a current signal under an action of the first multi-vibrator and the monostable trigger; and
   a first smart display, which is connected to an output of the time base circuit for displaying value of the current output signal.

2. The apparatus of claim 1, wherein the detector further comprises
   a memory unit for storing various parameters;
   a coding device for creating and scanning a QR code;
   a printing module, which is connected to the memory unit and the coding device, for printing the QR code and the parameters;
   an algorithm circuit module, which is connected to the memory unit, for accessing the parameters, for calculating grouting compactness distribution data in the grouted splice sleeve during grouting and curing;
   a 3-dimensional (3D) graphics display module, which is connected to the algorithm circuit module, for accessing and displaying the grouting compactness distribution data in 3D graphics; and
   a wireless data transmission module, which is connected to the 3D graphics display module, for wirelessly transmitting the 3D graphics of the grouting compactness distribution data to a mobile device or a computer.

3. An apparatus for detecting grout compactness in a grouted splice sleeve, comprising
   a probe assembly, wherein the probe assembly comprises at least a piezoelectric sensor for detecting a stress level in the grouted splice sleeve during grouting and is arranged inside the grouted splice sleeve to detect the stress level of the sleeve during grouting and curing; wherein the probe assembly have a coating made from hydrophobic material, i.e. modified polysilazane material; wherein the modified polysilazane material comprises 10 parts by weight of polysilazane, 0.4 parts by weight of silane coupling agent, 0.2 parts by weight of silica, and 0.08 parts by weight of perfluoropolyether;
   a first rubber plug at a top of the grouted splice sleeve;
   a second rubber plug at a grout outlet of the grouted splice sleeve;
   a rebar inside the grouted splice sleeve; wherein,
   the probe assembly is inserted into the grouted splice sleeve through the first rubber plug at the top of the sleeve; or
   the probe assembly is inserted into the grouted splice sleeve through the second rubber plug at the grout outlet of the sleeve; or
   the probe assembly is inserted into the grouted splice sleeve after being connected in parallel with the rebar;
   a detector; wherein
   the detector comprises at least a stress analysis module connected to the piezoelectric sensor, for calculation and analysis of stress value; wherein the stress analysis module comprises
   a time base circuit, which is connected to the piezoelectric sensor for obtaining resonance frequency signal;
   a second multi-vibrator, which is connected to the time base circuit, wherein the time base circuit outputs a voltage signal according to the resonance frequency signal under an action of the second multi-vibrator; and
   a second smart display, which is connected to an output of the time base circuit for displaying value of the voltage output signal.

4. The apparatus of claim 3, wherein the detector further comprises
   a memory unit for storing various parameters;
   a coding device for creating and scanning a QR code;
   a printing module, which is connected to the memory unit and the coding device, for printing the QR code and the parameters;
   an algorithm circuit module, which is connected to the memory unit for accessing the parameters for calculating grouting compactness distribution data in the grouted splice sleeve during grouting and curing;
   a 3-dimensional (3D) graphics display module, which is connected to the algorithm circuit module, for accessing and displaying the grouting compactness distribution data in 3D graphics; and
   a wireless data transmission module, which is connected to the 3D graphics display module, for wirelessly transmitting the 3D graphics of the grouting compactness distribution data to a mobile device or a computer.

5. A method for detecting grout compactness in a grouted splice sleeve, comprising the following steps,
  providing a probe assembly comprising at least a capacitive probe; inserting the probe assembly into the grouted splice sleeve with the capacitive probe arranged inside the grouted splice sleeve to detect a capacitance of the sleeve during grouting and curing; wherein inserting the probe assembly into the grouted splice sleeve further comprise at least one of the following steps,
  inserting the probe assembly into the grouted splice sleeve through a first rubber plug at a top of the grouted splice sleeve; or
  inserting the probe assembly into the grouted splice sleeve through a second rubber plug at a grout outlet of the grouted splice sleeve; or
  inserting the probe assembly connected in parallel with a rebar into the grouted splice sleeve;
  providing a predetermined threshold range on a detector, the detector comprises at least a capacitance analysis module that is connected with the probe assembly to obtain a capacitance and carry out calculation and analysis for the capacitance; wherein the capacitance analysis module comprises
  at least two time base circuits, which comprises a first time base circuit and a second time base circuit interconnected with each other, wherein the first time base circuit and the capacitive probe is connected to form a multi-vibrator;
  a first multi-vibrator, which is connected to the second time base circuit to form a monostable trigger, wherein the second time base circuit outputs a current signal under an action of the first multi-vibrator and the monostable trigger; and
  a first smart display, which is connected to an output of the time base circuit for displaying value of the current output signal;
  obtaining the capacitance of the grouted splice sleeve by the detector during grouting and curing;
  comparing the detected capacitance with the threshold range, the grouted splice sleeve will be determined as fully grouted if the detected capacitance is within the threshold range, whereas the grouted splice sleeve will be determined as defectively grouted if the detected capacitance is out of the threshold range;
  the method further comprises steps of determining the threshold range, including
  calculating a permittivity of the grout;
  obtaining an estimated capacitance value by calculation on the basis of the permittivity;
  obtaining a measured capacitance value detected by the capacitive probe after the grouted splice sleeves are grouted; and
  determining the threshold range in consideration of the calculated capacitance value and the measured capacitance value.

6. A method for detecting grout compactness in grouted splice sleeve, comprising the following steps,
  providing a probe assembly comprising at least a piezoelectric sensor; inserting the probe assembly into the grouted splice sleeve with the piezoelectric sensor arranged inside the grouted splice sleeve to detect a stress value of the sleeve during grouting and curing; wherein inserting the probe assembly into the grouted splice sleeve further comprise at least one of the following steps,
  inserting the probe assembly into the grouted splice sleeve through a first rubber plug at a top of the grouted splice sleeve; or
  inserting the probe assembly into the grouted splice sleeve through a second rubber plug at a grout outlet of the grouted splice sleeve; or
  inserting the probe assembly connected in parallel with a rebar into the grouted splice sleeve;
  providing a predetermined threshold range on a detector, the detector comprises at least a stress analysis module connected to the piezoelectric sensor to obtain the stress value and carry out calculation and analysis for the stress value; wherein stress the analysis module comprises
  a time base circuit, which is connected to the piezoelectric sensor for obtaining resonance frequency signal;
  a second multi-vibrator, which is connected to the time base circuit, wherein the time base circuit outputs a voltage signal according to the resonance frequency signal under an action of the second multi-vibrator; and
  a second smart display, which is connected to an output of the time base circuit for displaying value of the voltage output signal;
  obtaining the stress value of the grouted splice sleeve by the detector during grouting and curing;
  comparing the detected stress value with the threshold range, the grouted splice sleeve will be determined as fully grouted if the detected stress value is within the threshold range, whereas the grouted splice sleeve will be determined as defectively grouted if the detected stress value is out of the threshold range;
  the method further comprises steps of determining the threshold range, including
  obtaining an estimated resonance frequency by calculation after the piezoelectric sensor has been in contact with the grout;
  obtaining a measured resonance frequency detected by the piezoelectric sensor after the grouted splice sleeves are grouted;
  determining the threshold range of the resonance frequency in consideration of the estimated resonance frequency and the measured resonance frequency; and
  determining the threshold range of the stress value by converting the threshold range of the resonance frequency.

7. The method of claim 6, wherein the grouted splice sleeve is considered as fully grouted under the following conditions, including
  the detected parameter value is within the threshold range when grouting is finished; or
  the detected parameter value is within the threshold range when grouting is finished, but later it is restored to its level before grouting;
  whereas the grouted splice sleeve is considered as defectively grouted under the following conditions, including
  the detected parameter value is out of the threshold range when grouting is finished.

* * * * *